(12) United States Patent
Anderson et al.

(10) Patent No.: US 9,597,170 B2
(45) Date of Patent: *Mar. 21, 2017

(54) HYDRAULIC URETHRAL OCCLUSIVE DEVICE

(71) Applicant: GT UROLOGICAL, LLC, Minneapolis, MN (US)

(72) Inventors: David W. Anderson, Brooklyn Park, MN (US); Bernard J. Esarey, Avon, OH (US)

(73) Assignee: GT Urological, LLC, Minneapolis, MN (US)

( * ) Notice: Subject to any disclaimer, the term of this patent is extended or adjusted under 35 U.S.C. 154(b) by 88 days.

This patent is subject to a terminal disclaimer.

(21) Appl. No.: 14/453,026

(22) Filed: Aug. 6, 2014

(65) Prior Publication Data

US 2015/0045609 A1     Feb. 12, 2015

Related U.S. Application Data

(60) Provisional application No. 61/862,646, filed on Aug. 6, 2013, provisional application No. 61/909,781, filed on Nov. 27, 2013.

(51) Int. Cl.
*A61F 2/04* (2013.01)
*A61F 2/00* (2006.01)

(52) U.S. Cl.
CPC .................................. *A61F 2/004* (2013.01)

(58) Field of Classification Search
CPC ...... A61F 2/004; A61F 2/0004; A61F 2/0022; A61F 2/0027; A61F 2/0031;
(Continued)

(56) References Cited

U.S. PATENT DOCUMENTS

| 3,863,622 A | 2/1975 | Buuck |
| 4,222,377 A | 9/1980 | Burton |

(Continued)

FOREIGN PATENT DOCUMENTS

| CN | 1303253 | 7/2001 |
| CN | 101848685 | 9/2010 |

(Continued)

OTHER PUBLICATIONS

International Search Report and Written Opinion for International Application No. PCT/US2014/049930, dated Nov. 13, 2014, 16 pgs.

(Continued)

*Primary Examiner* — Charles A Marmor, II
*Assistant Examiner* — Thaddeus Cox
(74) *Attorney, Agent, or Firm* — Hamre, Schumann, Mueller & Larson, P.C.

(57) ABSTRACT

A totally implantable method for occluding the urethra or bladder neck utilizing an occlusive cuff connected to a control mechanism via a conduit tube. The occlusive cuff is reversibly changed from an activated (occlusive condition) to a deactivated (non-occlusive) condition by depressing a deactivation button contained within a resilient, elastomeric sheath surrounding the control mechanism. The occlusive condition is once again obtained by depressing an activation button also situated within the resilient sheath. In the occlusive condition, a preset tension is applied to a flexible diaphragm through a tensioning suture by a constant force spring contained within the control mechanism. This tension is translated into an occlusive pressure applied to the urethra or bladder neck sufficient to prevent urinary leakage.

19 Claims, 14 Drawing Sheets

(58) Field of Classification Search
CPC ............ A61F 2002/74; A61F 2002/745; A61F 2250/0003; A61F 2250/0013; A61M 2202/0496; A61M 2210/1078
See application file for complete search history.

(56) References Cited

U.S. PATENT DOCUMENTS

| | | | |
|---|---|---|---|
| 4,412,530 A | 11/1983 | Burton | |
| 4,419,985 A * | 12/1983 | Trick | A61F 2/0027 128/DIG. 25 |
| 4,632,114 A * | 12/1986 | Todd | A61F 2/004 128/DIG. 25 |
| 4,682,583 A | 7/1987 | Burton et al. | |
| 4,878,889 A | 11/1989 | Polyak | |
| 4,994,020 A | 2/1991 | Polyak | |
| 5,704,893 A | 1/1998 | Timm | |
| 6,074,341 A | 6/2000 | Anderson et al. | |
| 8,007,429 B2 | 8/2011 | Anderson et al. | |
| 2004/0147886 A1 * | 7/2004 | Bonni | A61F 2/004 604/327 |
| 2006/0264697 A1 * | 11/2006 | Timm | A61F 2/0036 600/29 |
| 2009/0012351 A1 * | 1/2009 | Anderson | A61B 17/1322 600/30 |
| 2010/0160716 A1 * | 6/2010 | Snow | A61F 2/004 600/31 |
| 2010/0211175 A1 | 8/2010 | Gomez-Llorens | |
| 2010/0331825 A1 | 12/2010 | Hakky et al. | |
| 2012/0011649 A1 * | 1/2012 | Ophaug | A61G 7/1023 5/81.1 T |

FOREIGN PATENT DOCUMENTS

| | | |
|---|---|---|
| DE | 9010783 | 9/1990 |
| WO | 2009094431 | 7/2009 |
| WO | 2013158586 | 10/2013 |

OTHER PUBLICATIONS

"AMS800 Artificial Urinary Sphincter," American Medical Systems, Inc. 2009, 4 pgs.
"FlowSecure: Artificial Urinary Sphincter," Sphinx Medical, At least as early as Apr. 2013, 4 pgs.
"Male Continence: An Artificial Urinary Sphincter Update," Supplement to Urology Times, Aug. 2011, 12 pgs.
Extended European Search Report for application No. 14835202.4, dated Nov. 28, 2016 (8 pages).
Office Action issued for Chinese patent application No. 201480044663.1, dated Jan. 11, 2017 (19 pages, including English translation).

* cited by examiner

HYDRAULIC URETHRAL OCCLUSIVE DEVICE

This invention was made with government support under SBIR Grant Number R43 DK092007-01 awarded by the National Institutes of Health. The government has certain rights in the invention.

FIELD

The disclosure herein relates to embodiments of a hydraulic urethral occlusive devices (HUOD) that are entirely inserted or surgically implanted within the body for controlling the lack of urinary or bowel restraint. These devices are commonly referred to as "artificial sphincters" which are installed within the body to aid or replace the body's natural sphincter.

BACKGROUND

One such device by American Medical Systems, Inc. is the AUS 800, which is a totally implantable hydraulic sphincter implanted in both males and females experiencing urinary incontinence and has been on the market for over 35 years. The AUS 800 and its predecessors are described in U.S. Pat. Nos. 3,863,622; 4,222,377; 4,412,530; and 4,878,889. The AUS 800 consists of a silicone pressure regulating balloon implanted in the prevesical space, a silicone control pump implanted in the scrotum or labia, and a silicone urethral occlusive cuff wrapped around the bulbous urethra in males or bladder neck in females. Each component is filled with saline or radiopaque contrast media. Tubing, emanating from each component, is routed between incisions and appropriate connections are made. The device is deactivated for a period of approximately 6 weeks to allow tissue healing to proceed and urethral edema to subside. At activation, the control pump is squeezed sharply to unseat a poppet and open operational fluid flow paths. The patient is taught to operate the device by squeezing the control pump through the scrotal or labial skin. This action transfers fluid from the cuff to the pressure regulating balloon. The balloon forces the fluid through a fluid restrictor and back into cuff to reestablish an occlusive urethral pressure within 3-5 minutes. The AUS 800 is complicated to implant, is prone to fluid leakage, and causes urethral atrophy and erosion. Despite these draw backs, the AMS 800 is the only commercially available artificial urinary sphincter.

Another such type of mechanical artificial urinary sphincter, the Timm-AUS, is described in U.S. Pat. Nos. 5,704,893 and 6,074,341, both of which are entitled VESSEL OCCLUSIVE APPARATUS AND METHOD. The Timm-AUS is a one piece device not requiring saline filling or intra-operative assembly. Depression of a deactivation button through the scrotal skin causes a urethral occlusive sheath to expand and remove occlusive pressure from the urethra to allow normal urination. Depression of an activation button allows the occlusive sheath to contract and reapply urethral pressure to prevent urethral leakage. Human implantation experience with the Timm-AUS was hindered by formation of a tough, fibrous capsule surrounding the device which prevented expansion of the Occlusive Sheath.

Another mechanical method of occluding the urethra is demonstrated by U.S. Pat. No. 8,007,429 A1 entitled VESSEL OCCLUSIVE DEVICE AND METHOD FOR OCCLUDING A VESSEL. In this patent, depression of an activation button allows a constant force spring to apply tension to a compressible tape wrapped circumferentially about the urethra. In so doing, urinary leakage is prevented. Depressing a deactivation button removes spring tension and urethral compression to allow unobstructed urinary voiding.

A hybrid mechanical/hydraulic artificial urethral sphincter is described in US patent application publication 2010/0211175 A1 SURGICAL IMPLANT, IN PARTICULAR ARTIFICIAL SPHINCTER WITH ADJUSTED PRESSURE. This patent application publication describes a helical spring biased piston which maintains hydraulic pressure within an inflatable cuff circumferentially disposed about the urethral circumference. Depression of a secondary hydraulic bladder forces fluid from the piston into a third holding bladder to remove hydraulic pressure from the urethra. The pressurized fluid within this third bladder is then slowly discharged back into the piston through a fluid restrictor to re-establish hydraulic pressure about the urethra. Pressurized fluid may be locked out of the hydraulic cuff to remove pressure for a prolonged period as might be required immediately following implantation and during sleep when urinary leakage is not as problematic. Lockout is accomplished by depressing a lockout button. Returning the device to its normal function is accomplished by depressing the lockout button on its opposite side.

As evidenced by clinical experience with the above devices, it is difficult to teach the patient to identify and then operate the small lockout valve which is encased within and masked by scrotal tissues. Additionally, cuff refilling through the fluid restrictor takes 3 to 5 minutes. This allows ample time for the patient to believe that his bladder is empty and leave the commode. Residual urine within the bladder may then leak through the uncompressed urethra to wet the patient's clothing.

SUMMARY

A hydraulic urethral occlusive device (HUOD) is described herein that is an implantable artificial urinary sphincter intended to provide the incontinent patient protection against urine leakage and "at will" control over his/her voiding function. The HUOD is intended to address the drawbacks of the state of the art by providing several features described herein and illustrated in the drawings.

DRAWINGS

These and other features, aspects, and advantages of the hydraulic urethral occlusive device will become better understood when the following detailed description is read with reference to the accompanying drawing, wherein.

1, according to one embodiment, and shown in a state when the hydraulic urethral occlusive device is off, unpressurized. FIG. 5B is a lateral sectional view of the pressure compensator of FIG. 5A in the state when the hydraulic urethral occlusive device is off, unpressurized. FIG. 5C is a frontal sectional view of the pressure compensator of FIG. 5A, and shown in a state when the device is on, pressurized. FIG. 5D is a lateral sectional view of the pressure compensator of FIG. 5A in the state when the hydraulic urethral occlusive device is on, pressurized.

Figure 1:
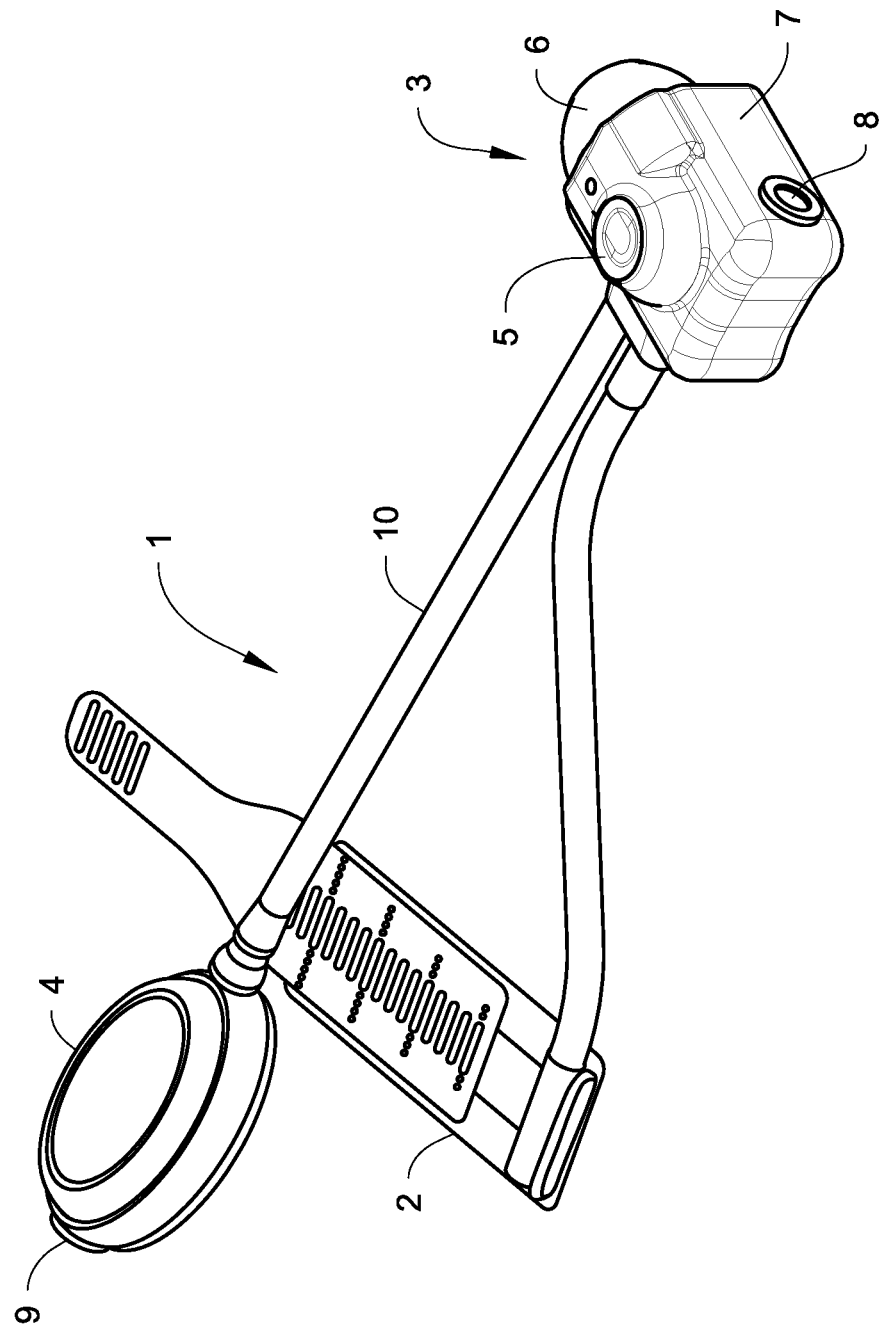
FIG. 1 is a perspective view of a hydraulic urethral occlusive device according to one embodiment, and shown with one embodiment of an occlusive cuff not encircling a urethra.
Figure 6A:
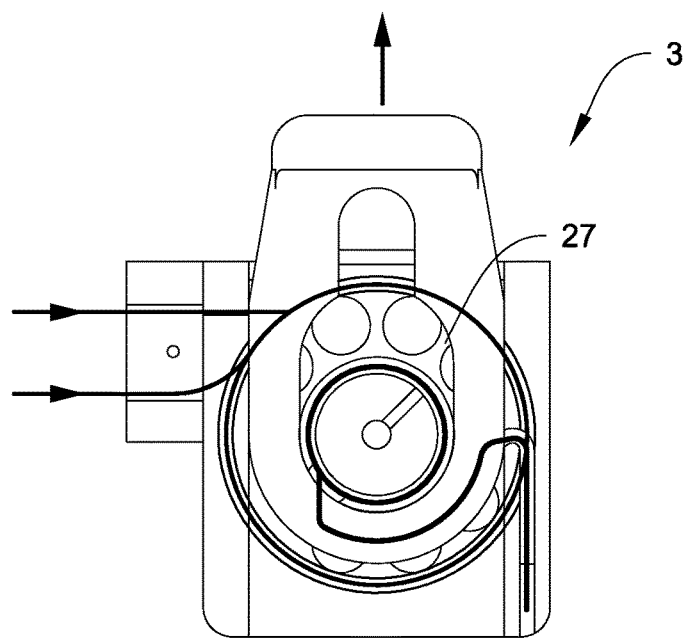
Figure 6B:
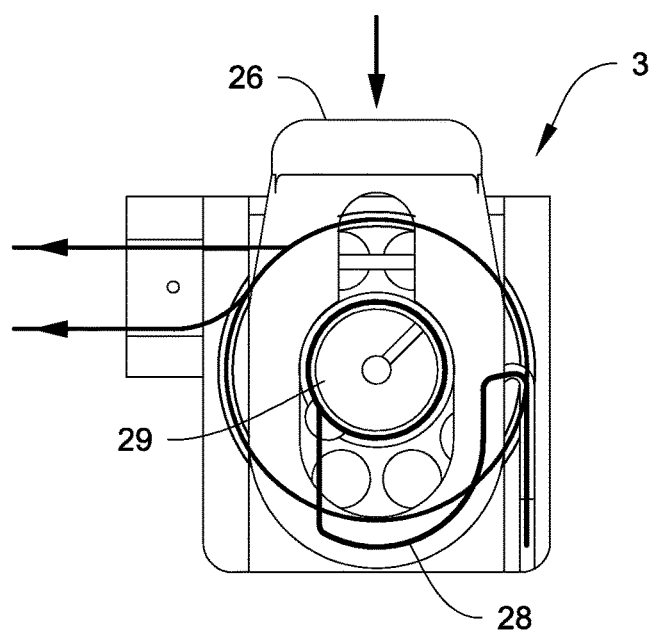

FIG. 6A is a side view of a control mechanism of the hydraulic urethral occlusive device of FIG. 1, according to one embodiment, and shown in a state when the hydraulic urethral occlusive device is activated. FIG. 6B is another side view of the control mechanism of the hydraulic urethral occlusive device of FIG. 6A, and shown in a state when the hydraulic urethral occlusive device is deactivated.

Figure 7A:
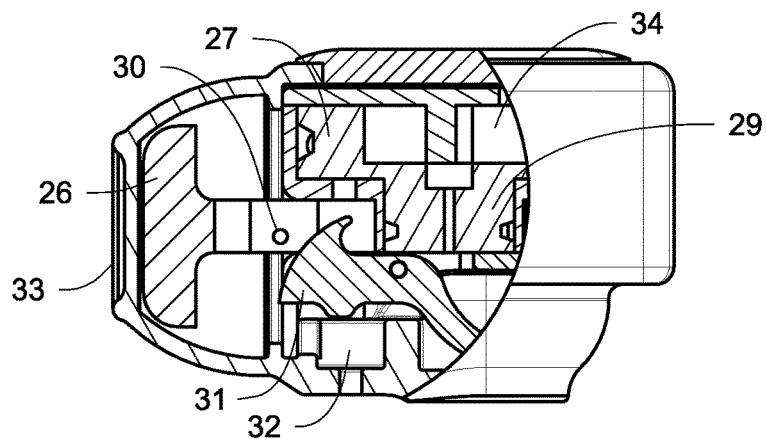
Figure 7B:
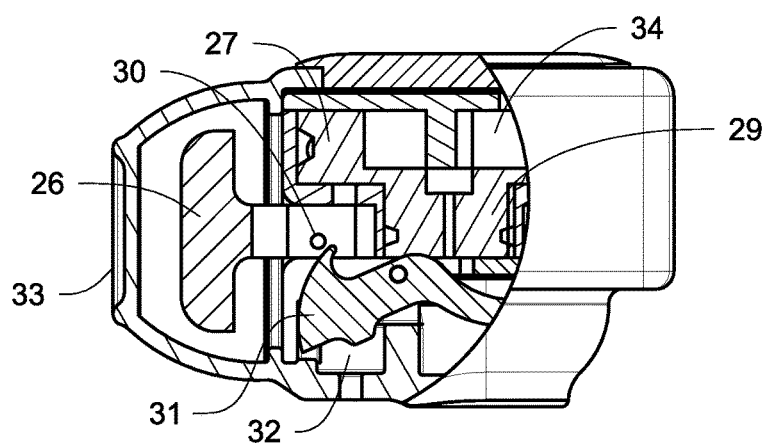
Figure 7C:
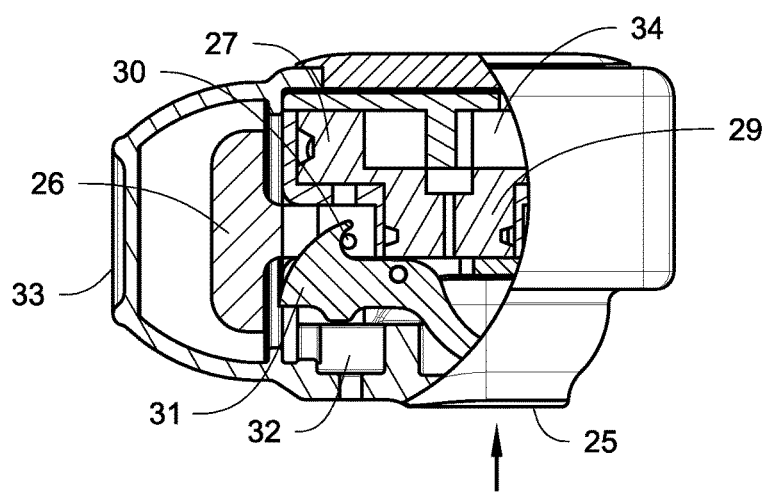

FIG. 7A is a side sectional view of the control mechanism of FIG. 6A, shown in the activated state. FIG. 7B is a side sectional view of the control mechanism of FIG. 6A, shown moving to the deactivated state. FIG. 7C is a side sectional view of the control mechanism of FIG. 6A, shown in the deactivated state.

Figure 8:
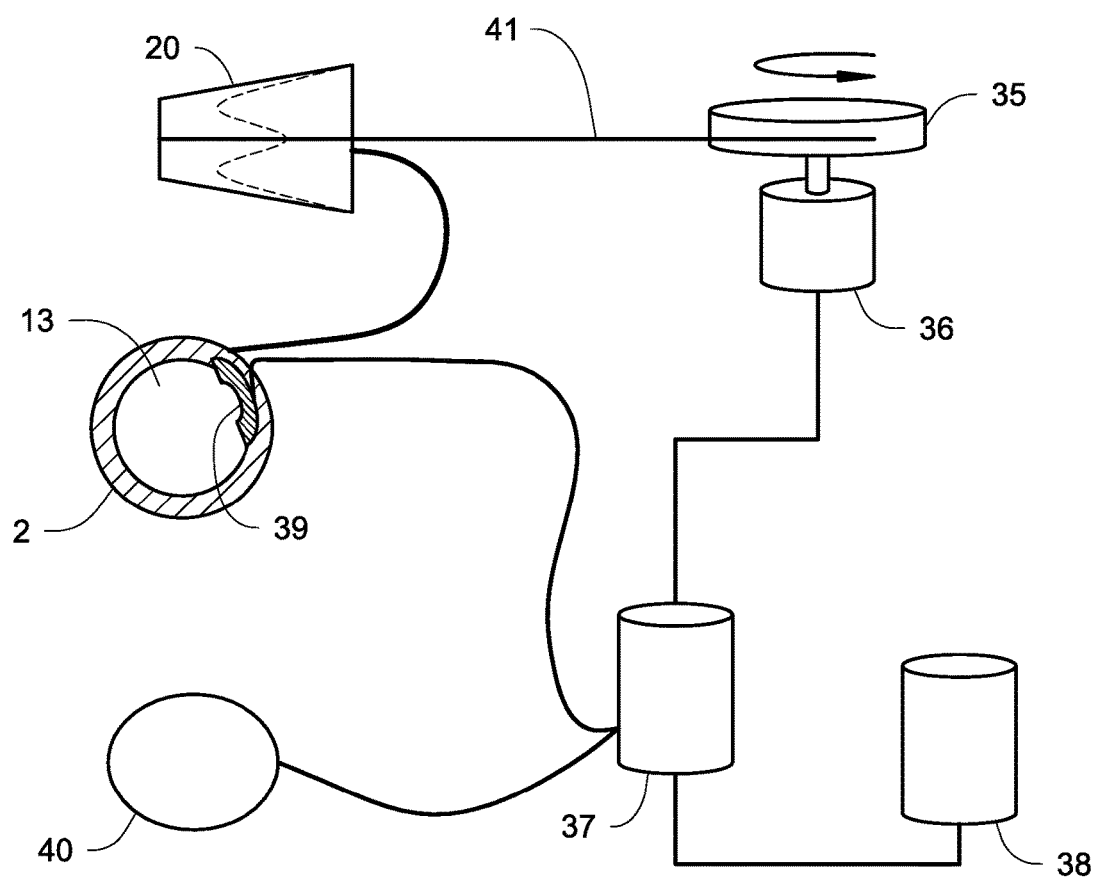

FIG. 8 is diagrammatic view of a hydraulic urethral occlusive device, according to another embodiment, in which the control mechanism is an electro-mechanical control mechanism.

Figure 9:
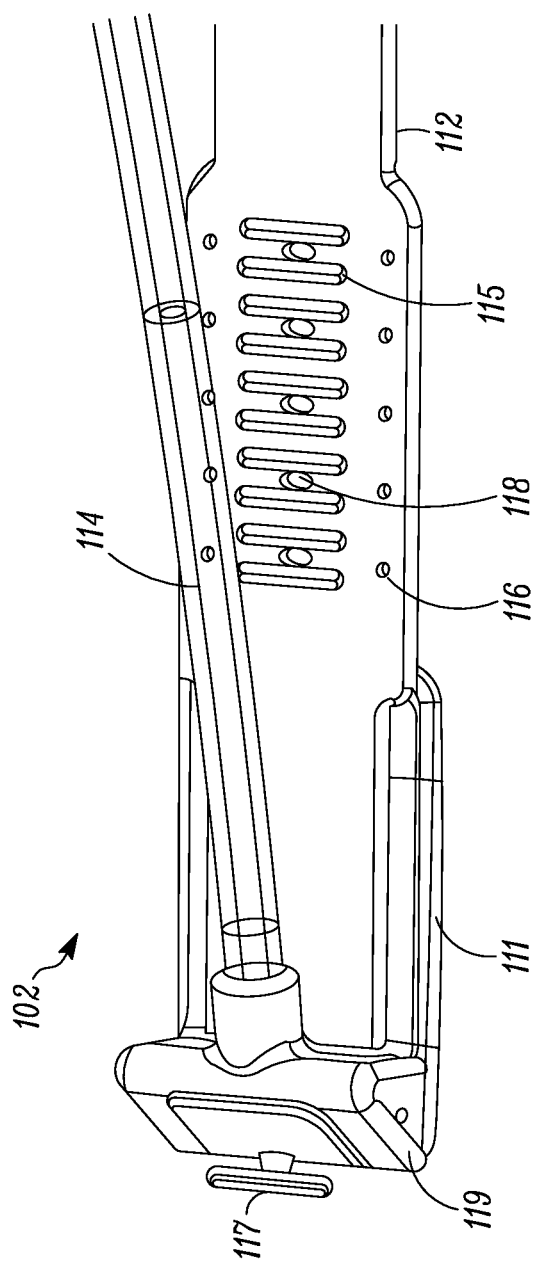

FIG. 9 is a perspective view of another embodiment of an occlusive cuff not encircling a urethra and shown in a flat condition.

Figure 10A:
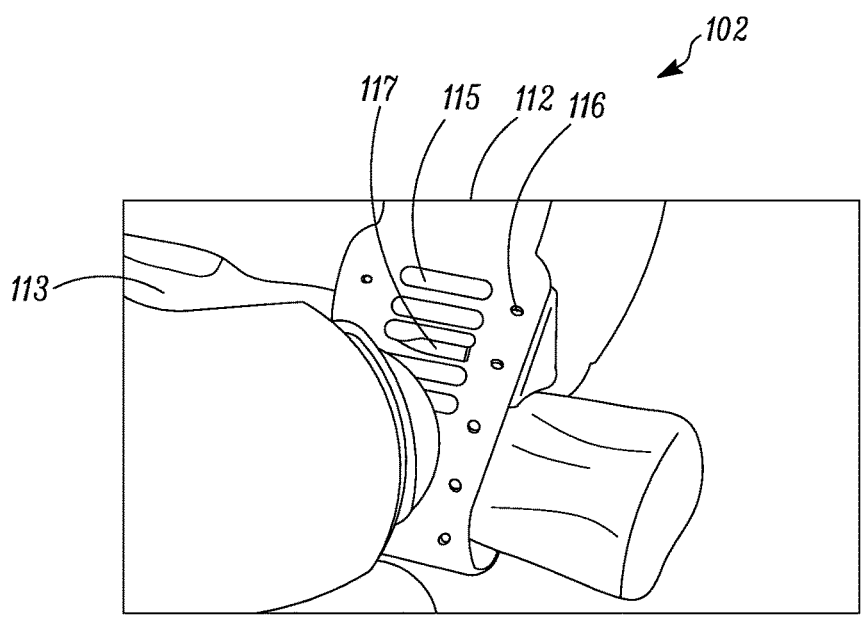

FIG. 10A is a partial view showing the occlusive cuff of FIG. 9 shown encircling a urethra but not in the fully clipped position.

Figure 10B:
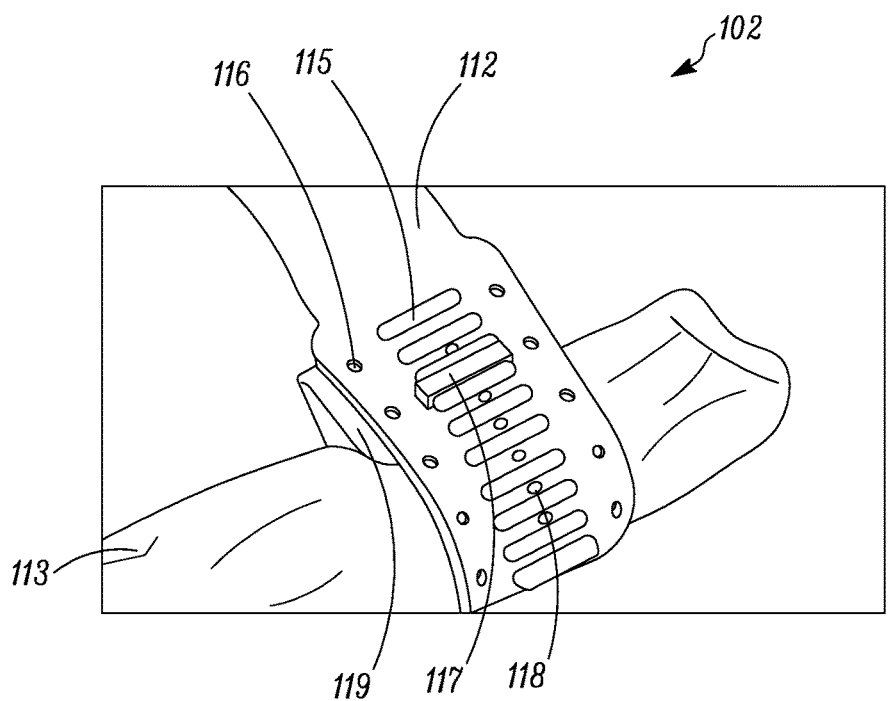

FIG. 10B is a partial view showing the occlusive cuff of FIG. 9 shown encircling a urethra in the fully clipped position.

Figure 11:
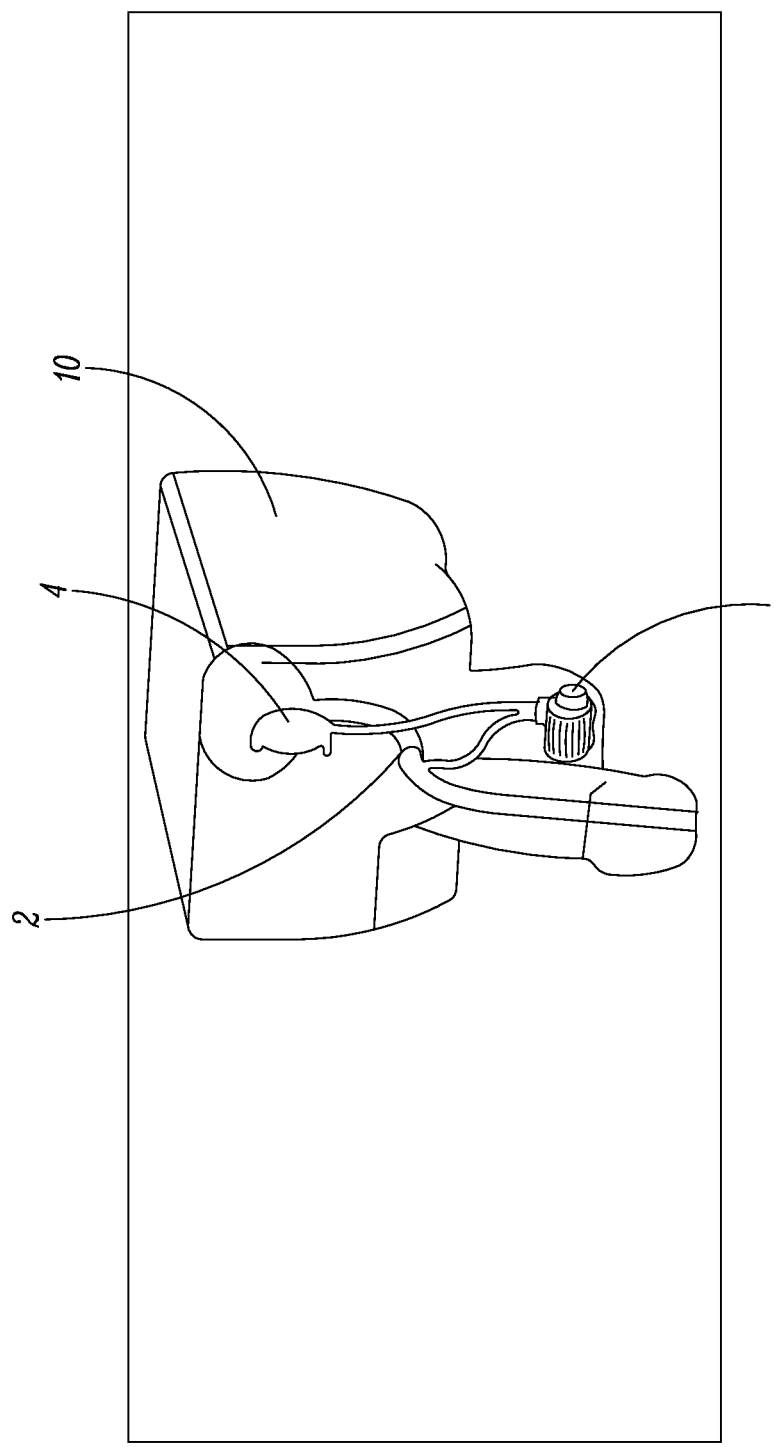

FIG. 11 is a schematic view of one embodiment of a hydraulic urethral occlusive device implanted in a human male subject.

Figure 12B:
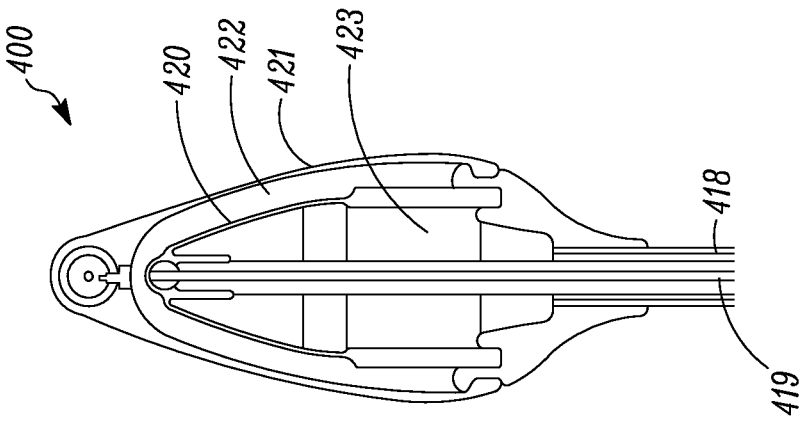
Figure 12A:
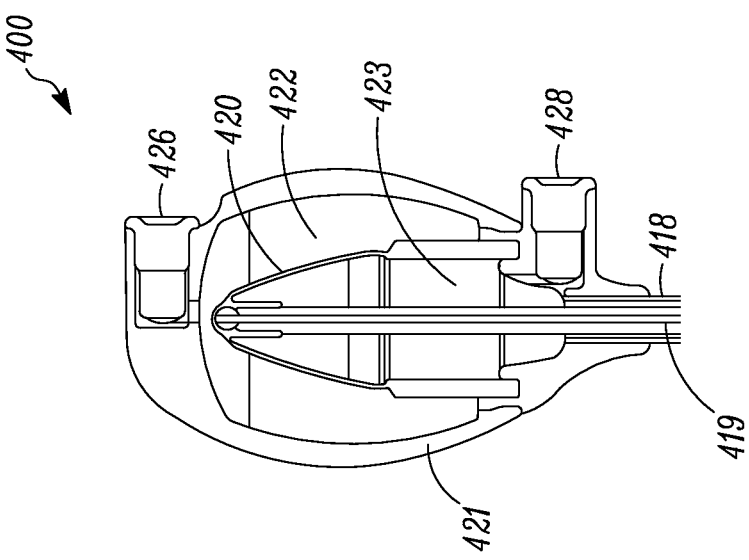
Figure 12D:
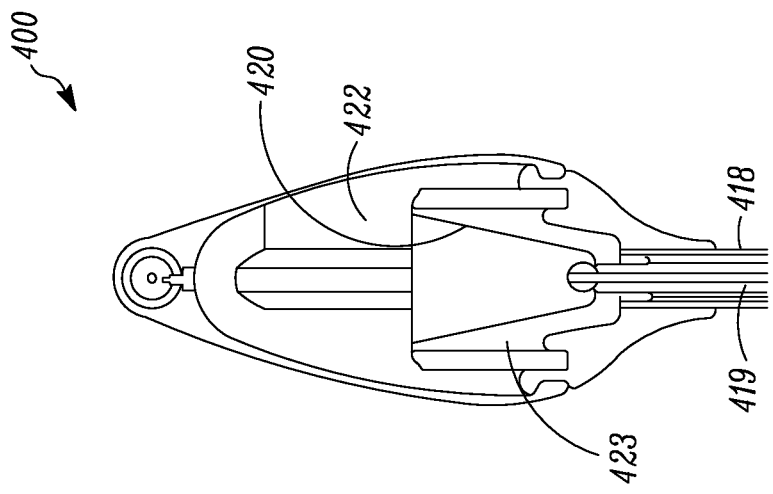
Figure 12C:
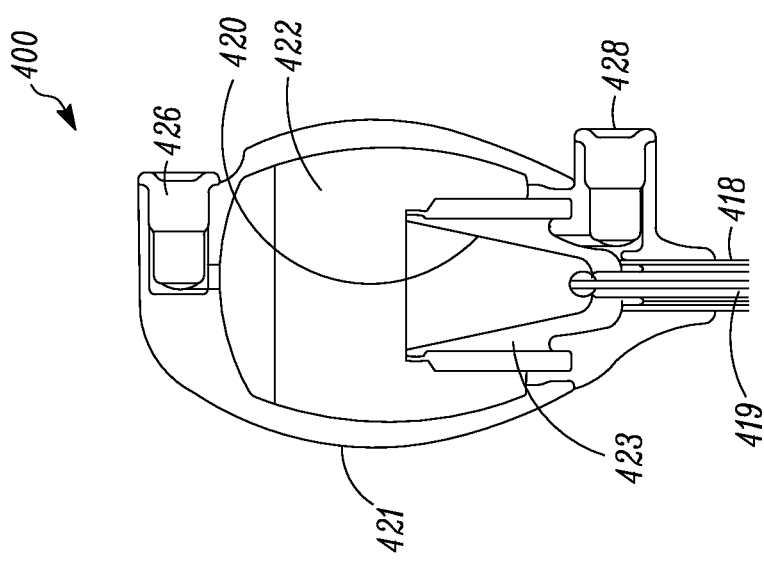

FIGS. 12A to 12D show views of another embodiment of a pressure compensator with a hollow shell, which may be flexible and which may be resilient. FIG. 12A is a frontal sectional view of the pressure compensator shown in a state when the hydraulic urethral occlusive device is off, unpressurized. FIG. 12B is a lateral sectional view of the pressure compensator of FIG. 12A in the state when the hydraulic urethral occlusive device is off, unpressurized. FIG. 12C is a frontal sectional view of the pressure compensator of FIG. 12A, and shown in a state when the device is on, pressurized. FIG. 12D is a lateral sectional view of the pressure compensator of FIG. 12A in the state when the hydraulic urethral occlusive device is on, pressurized.

Figure 13B:
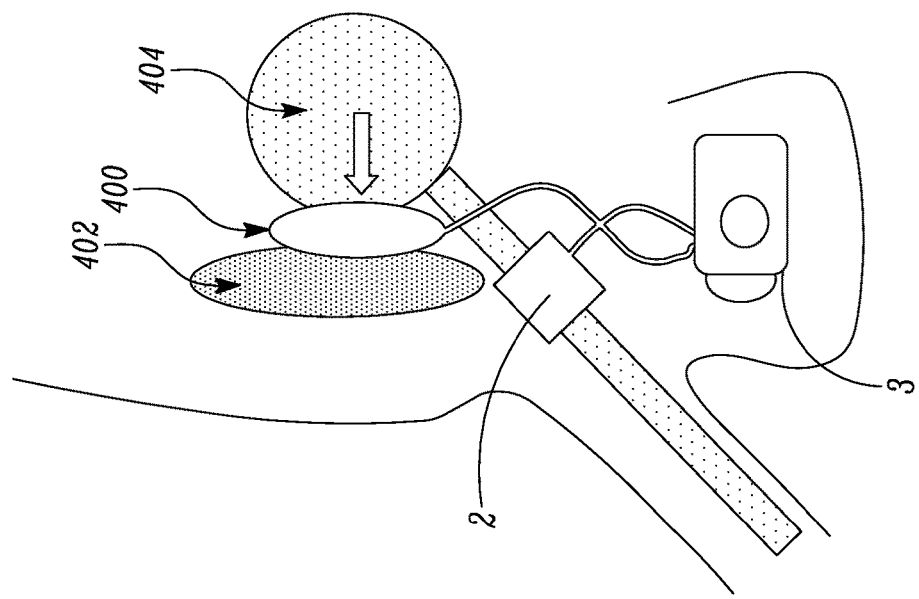
Figure 13A:
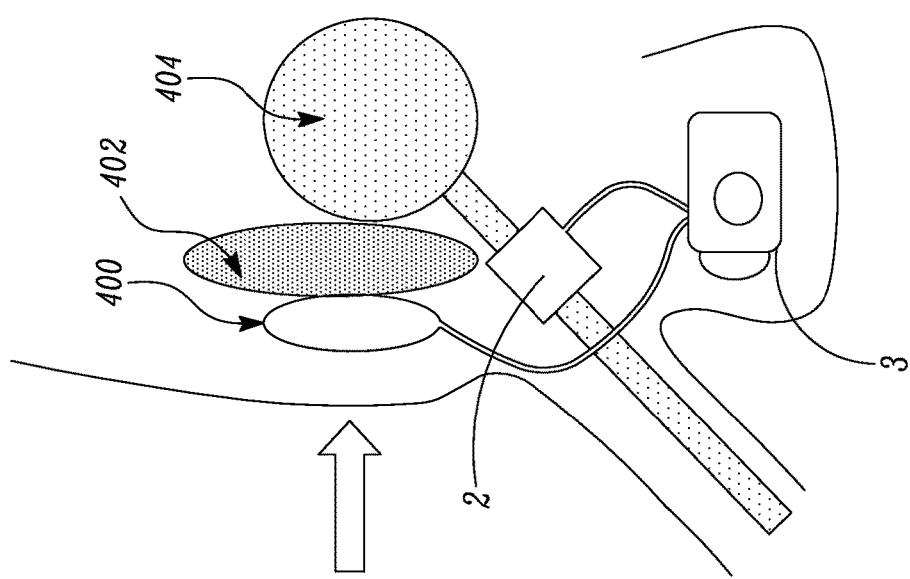

FIGS. 13A and 13B show embodiments of a hydraulic urethral occlusive device implanted in a human male subject, and which may implement the pressure compensator of FIGS. 12A to 12D. FIG. 13A shows the pressure compensator placed in a subcutaneous location, such as in the abdominal subcutaneous tissue. FIG. 13B shows the pressure compensator placed in a pre-vesical space, such as between the bladder and the pubic bone.

Figure 14:
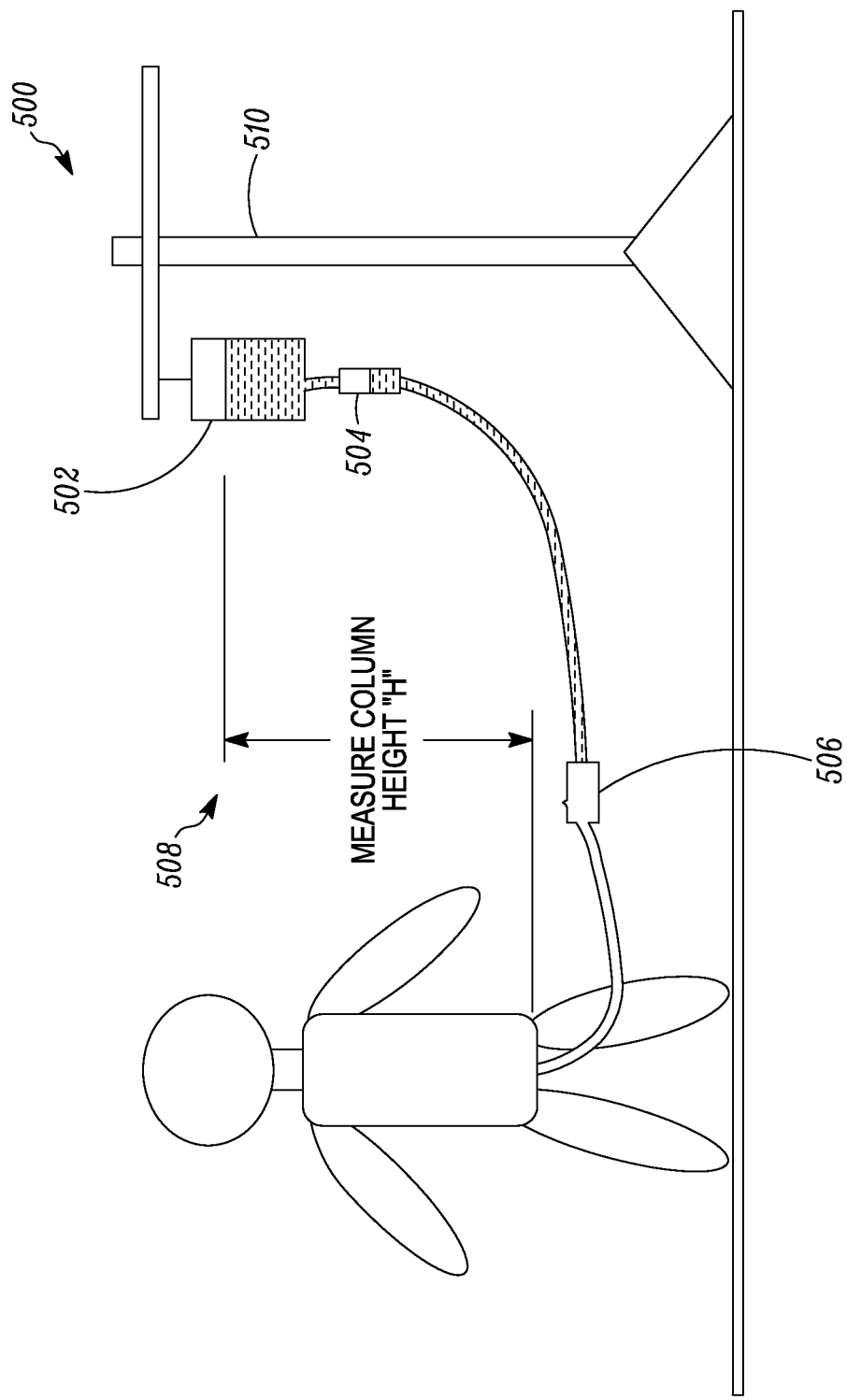

FIG. 14 shows one embodiment of post-implantation adjustment, such as by retrograde perfusion, to for example increase or decrease occlusive pressure.

While the above-identified figures set forth particular embodiments of the hydraulic urethral occlusive device, other embodiments are also contemplated, as noted in the discussion. In all cases, this disclosure presents illustrated embodiments of the hydraulic urethral occlusive device by way of representation but not limitation. Numerous other modifications and embodiments can be devised by those skilled in the art which fall within the scope and spirit of the principles of the heat recovery systems and methods described herein.

DETAILED DESCRIPTION

A hydraulic urethral occlusive device (HUOD) 1, as depicted for implantation in males is illustrated in FIG. 1. The hydraulic urethral occlusive device is a one-piece device implanted through a single perineal or peno-scrotal incision. An inflatable hydraulic occlusive cuff 2 encircles the urethra and is permanently attached via a flexible tube to the control mechanism 3 implanted in the scrotum. A pressure compensator 4 is likewise permanently attached to the control mechanism 3 via a flexible conduit 10 to allow placement in the subcutaneous tissues of the abdomen, thigh or alternately in the pre-vesical space. The occlusive cuff 2 is implanted in an uninflated, deactivated condition for approximately 6 weeks post-operatively to facilitate healing and allow pain and edema to subside. Following this deactivation period, the urologist activates the device by depressing an activation button 5 through the intact scrotal skin. In so doing, the occlusive cuff 2 inflates to apply a preset occlusive pressure within the range of 60-80 cm $H_2O$ to the urethra. The patient is then free to depress a deactivation button 6 to evacuate hydraulic fluid from the occlusive cuff 2 and allow unobstructed voiding. To re-establish urethral occlusive pressure and continence, the patient pushes the activation button 5.

The control mechanism 3 is encapsulated by a silicone boot 7 which incorporates a needle port or septum 8. All other HUOD components likewise can be encapsulated by silicone rubber coverings to prevent hydraulic solution leakage and the incursion of bodily fluids. The control mechanism 3 is in fluid communication with the occlusive cuff 2 and the inner portion of the pressure compensator 4. The inner portion of the pressure compensator 4 is further surrounded by an outer pressure capacitor chamber containing a second and separate fluid volume. This chamber also incorporates a needle puncture port or septum 9. Each separate fluid volume defined by the above-mentioned structures may be filled by accessing each septum 8 and 9 with a hypodermic needle and infusing appropriate filling solutions. The pressure compensator 4 and control mechanism 3 are joined by the flexible conduit 10.

The first fluid volume contained within the control mechanism 3, occlusive cuff 2, and the inner portion of the pressure compensator 4 is filled with normal saline or radiopaque solutions intended to allow visualization of these otherwise, non-radiopaque structures. The outer pressure capacitor chamber is filled with normal saline only, so as not to obscure radiographic visualization of the inner portion of the pressure compensator 4.

The occlusive cuff 2 may be adjusted to accommodate varying urethral circumferences as might be found in the human population. The urethral circumference may first be measured with a flexible measuring tape. The cuff 2 is then wrapped around the urethra and locked into a detent corresponding to the measured urethral circumference.

The hydraulic urethral occlusive device is also configurable for female implantation through a transvaginal or abdominal incision. In this case, the occlusive cuff 2 would encircle the bladder neck or mid-urethra. The control mechanism 3 for female implantation would be miniaturized for implantation in the labia or abdominal skin where it could be operated by manual depression activation and deactivation buttons 5, 6, through the labial or abdominal tissue. The pressure compensator 4 may be implanted in similar locations described for male implantation. The control mechanism 3 may also be replaced with a motor driven servo which would alternately apply or remove tension from the pressure compensator causing it to apply or remove pressure from the cuff 2 (see e.g. embodiment of FIG. 8 further described below). The addition of implantable pressure transducing elements and a closed-loop control system would allow this device to respond in real-time to increases in bladder and, or intra-abdominal pressures which may cause the patient to leak urine (see e.g. embodiment of FIG. 8 further described below).

Advantages over the current state of the art can include, for example:

no intra-operative assembly required;

no tubing connectors which are prone to disconnection;

allows post-implantation re-pressurization to allow degree of continence to be incrementally improved;

single incision implantation with reduced surgical morbidity;

a "one size fits all" cuff design which eliminates the need for a hospital to stock devices in a multitude of sizes which are then selected at the time of surgery;

greatly reduced operative time as evidenced by human implants with predecessor device;

large buttons which are easily identifiable and operable by both physician and patient without the need for a separate deactivation button; and no time delay when changed from the deactivated to activated conditions to reduce unexpected urinary leakage.

The hydraulic urethral occlusive device also has applications in the areas of fecal incontinence, gastro-esophageal reflux disease (GERD), and gastric banding for weight loss. Other disease states which may be served by occlusion or support of tubular body passages may lend further usage to the HUOD concept.

As described above, the hydraulic urethral occlusive device is a totally implantable artificial urinary sphincter intended to prevent urinary leakage in both males and females. Men frequently become incontinent of urine following surgeries to remove cancerous prostates. Women are often rendered incontinent due to the pelvic trauma caused during childbirth and due to a laxity of the pelvic muscles occurring due to aging. To a lesser degree, men and women are rendered incontinent due to trauma, infection and birth defects. The American Medical Systems, Inc. AUS 800 is the only commercially available, totally implantable artificial urinary sphincter. The complexity of its implantation is due to the requirement to intra-operatively fill and assemble its three components. The AUS 800 often fails due wear in its componentry which leads to fluid leakage and post-operative infections. Urethral atrophy and erosion sometimes occur and are suspected to be due to the crenate shape of its occlusive cuff. The AUS 800 is available with a number of occlusive pressure ranges with 61-70 cm $H_2O$ being the pressure most frequently selected.

Referring back to FIG. 1, the hydraulic urethral occlusive device 1 is a one-pieced device not requiring assembly. The hydraulic urethral occlusive device 1 may be filled with saline solution, or a combination of saline solution and radiopaque dyes intended to aid in visualization of anatomical placement and functionality. The hydraulic urethral occlusive device has the occlusive cuff 2 to surround the urethra or bladder neck and has the control mechanism 3, which is implanted in the scrotum in males and the labia or abdominal wall in females. The pressure compensator 4 is joined to the control mechanism 3 by the conduit 10 through which tensioning cables pass (see e.g. FIGS. 5A through 5D). The conduit 10 is flexible to accommodate bodily movement by the human implant subject.

Occlusive Cuff

Figure 2:
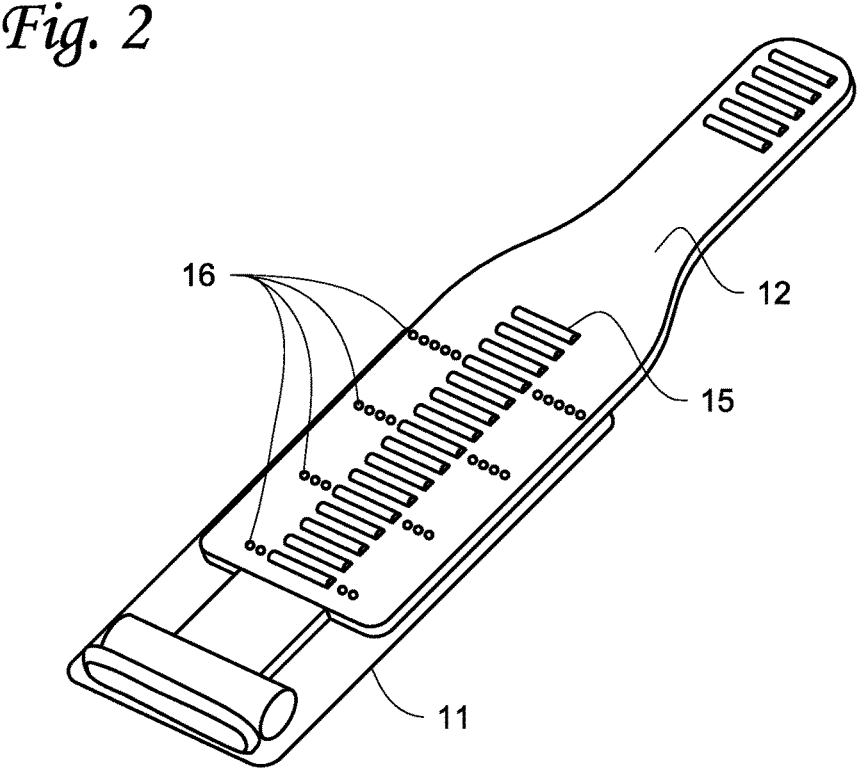
FIG. 2 is a perspective view of the occlusive cuff alone from the hydraulic urethral occlusive device of FIG. 1, shown in a flat condition.
Figure 3:
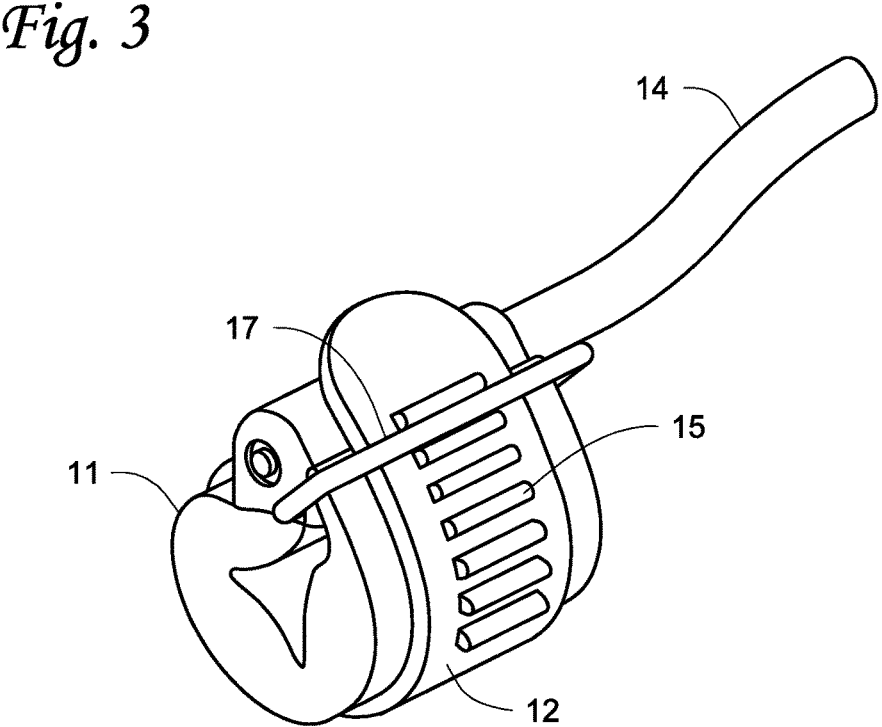
FIG. 3 is perspective view of the occlusive cuff alone from the hydraulic urethral occlusive device of FIG. 1, shown encircling a urethra.
Figure 4A:
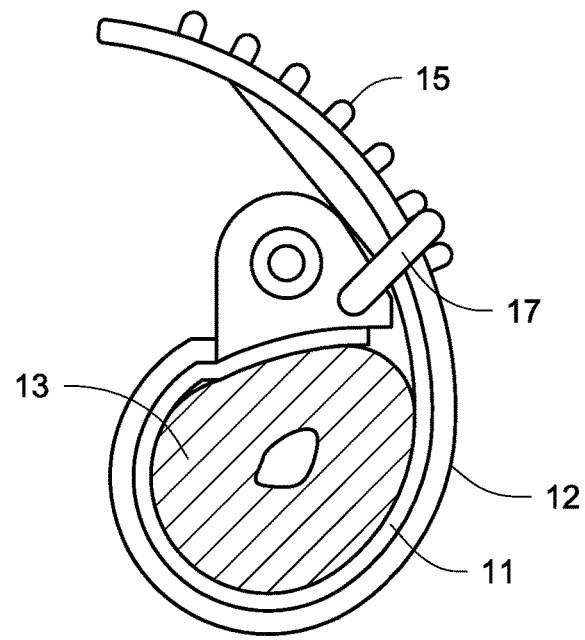
FIG. 4A is a side view of the occlusive cuff of alone from hydraulic urethral occlusive device of FIG. 1, shown sized around a relatively smaller urethra.
Figure 4B:
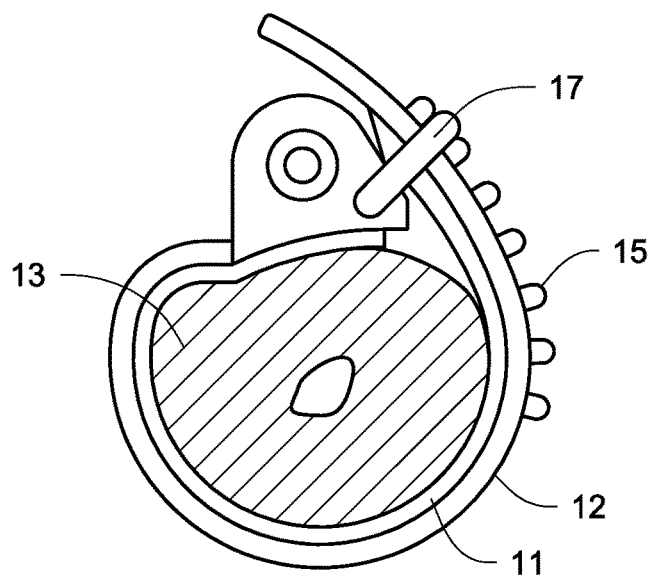
FIG. 4B is a side view of the occlusive cuff of alone from hydraulic urethral occlusive device of FIG. 1, shown sized around a relatively larger urethra.

Further details of the occlusive cuff 2 are shown in FIGS. 2-4. FIG. 2 shows the occlusive cuff 2 in its flat condition prior to implantation and in its condition when it could encircle a urethra 13 in FIGS. 3 and 4. The occlusive cuff has a thin-walled, expandable pouch 11 to which is affixed a semi-flexible cuff backing strip 12 as shown in FIG. 2. When encircling the urethra 13 (see e.g. FIGS. 4A and 4B), the fluid-tight expandable pouch 11 may be alternately expanded or deflated by infusion of a suitable filling media such as isotonic saline or radiopaque contrast media. Inflation occurs through a flexible input tube 14, such as indicated in FIG. 3. The occlusive cuff 2 with the expandable pouch 11 inflated is also shown in FIG. 3. When the expandable pouch 11 is inflated, the pressure exerted on the urethra 13 is sufficient to prevent or minimize urinary leakage. Historical clinical evidence suggests that this pressure should be in the range of 60-80 cm $H_2O$ to provide adequate leak resistance without causing undue urethral atrophy or tissue erosion. When the expandable pouch 11 is deflated, pressure is removed from the urethra 13 to allow normal, unobstructed urinary drainage. The cuff backing strip 12 is positioned on the expandable pouch 11 surface away from the urethral surface and acts to maximize urethral occlusion efficiency by minimizing radial expansion of the expandable pouch 11 away from the urethra 13. Sizing Detents 15 are positioned on the cuff backing strip 12 to allow the occlusive cuff 2 to be sized to accommodate anatomical variations in urethral circumferences as may occur in the human population as shown in FIGS. 4B and 4B. Clinical experience indicates that the range of urethral circumferences in the human male population ranges from 3.5 cm to 5.0 cm. Sizing indicators 16 may be associated with the detents 15 to provide the surgeon with urethral circumference information. When the occlusive cuff 2 is surgically wrapped around the urethra 13, the free end of the occlusive cuff 2 is inserted through a locking clip 17 and advanced to the detent 15 to provide a close fit between the occlusive cuff 2 and urethra 13.

FIGS. 9 and 10A to 10B show another embodiment of retaining and/or locking the occlusive cuff in place, which is further described below.

The expandable pouch 11 may be constructed using an inner substrate of expanded polytetrafluoroethylene (ePTFE). The substrate may be in tubular form, sealed at either end to form a leak-proof pouch. The flat width of the tubular expandable pouch 11 may be within the range of 1 cm to 3 cm and ePTFE materials with a wall thickness of 0.003"-0.005" and an internodal distance (porosity) of 30μ-50μ have been shown to have an appropriate flexibility. The substrate is rendered leak-proof by application of a thin coat of silicone rubber applied by a dispersion dip molding process. The ePTFE porosity range indicated above, allows deposition of silicone dispersion into the porous interstices to create a bond between the silicone outer layer and the ePTFE substrate. Wear and subsequent filling media leakage is minimized by applying low coefficient of friction coatings to the opposing outer silicone surfaces. These coatings include polytetrafluoroethylene (PTFE) particulate oversprays or NuSil MED 6670 or NuSil MED 6671 silicone dispersions. Wear created by relative movement of opposing surfaces on the inner of the expandable pouch 11 surfaces is minimized by the low coefficient of friction nature of the ePTFE substrate.

Alternately, the expandable pouch 11 may be entirely manufactured from silicone using a dispersion casting or molding method. To reduce the tendency of wear induced holes in the expandable pouch 11, polytetrafluoroethylene (PTFE) particulate over-sprays or NuSil MED 6670 or NuSil MED 6671 silicone dispersions may be used as coatings on the inner and outer surfaces of the expandable pouch 11.

Pressure Compensator

In FIGS. 5A to 5D, the pressure compensator 4 is a structure attached to the control mechanism 3 via a flexible conduit tube 18, 10. A tension cord 19 travels from the control mechanism 3 through the conduit tube 18 to the apex of the pressure compensator diaphragm 20. The pressure compensator diaphragm 20 is a thin-walled, bullet-shaped diaphragm which operates between an expanded and collapsed condition. Tension applied to the tension cord 19 by the control mechanism 3 collapses the pressure compensator diaphragm 20, and pressurizes the filling media contained within it (see e.g. FIGS. 5B and 5C). This filling media volume is then transferred to the occlusive cuff 2 which inflates to occlude the urethra. The pressure generated within the pressure compensator diaphragm 20 is determined by its cross-sectional area and the force applied to the tension cord 19 according to the equation:

Pressure=Force/Cross-sectional Area

Figure 5A:
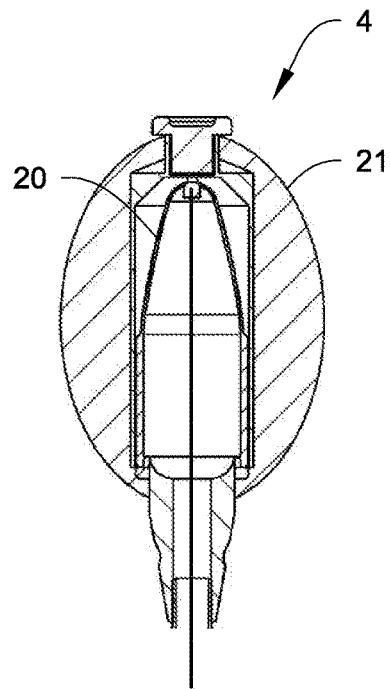
FIG. 5A is a frontal sectional view of a pressure compensator of the hydraulic urethral occlusive device of FIG.
Figure 5B:
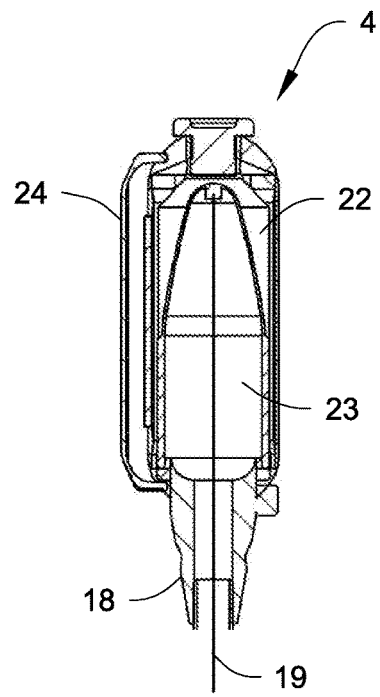
Figure 5C:
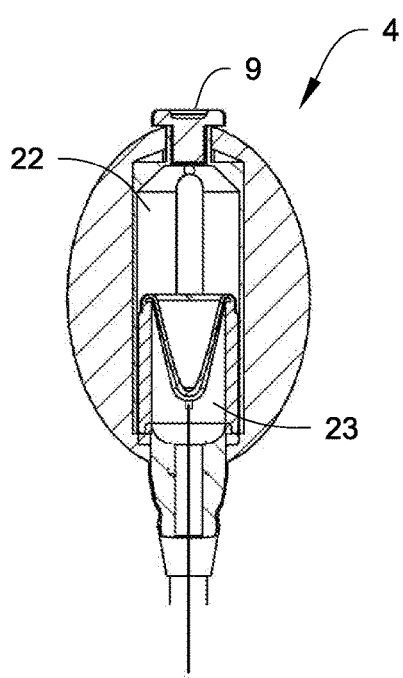
Figure 5D:
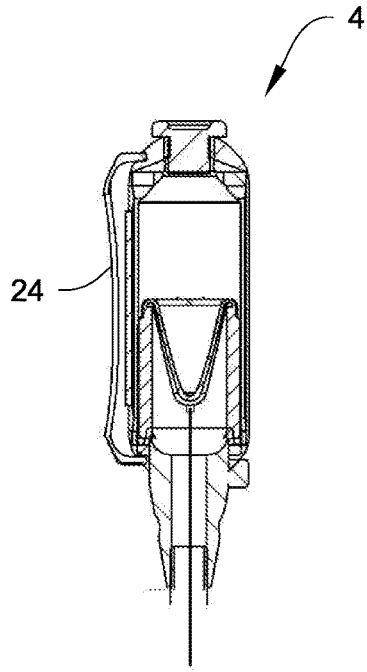

When tension is released from the tension cord 19, the resilience of the compressed urethral tissue forces filling media out of the occlusive cuff 2 and re-expands the pressure compensator diaphragm 20 to the position shown in FIGS. 5A and 5B.

The pressure compensator diaphragm 20 is contained within a semi-rigid compensator shell 21 which prevents surrounding bodily tissue from collapsing around and applying unintended pressure to the pressure compensator diaphragm 20. A fluid volume 22 contained within the compensator shell 21 surrounds and is separated from the filling media volume 23 contained within the pressure compensator diaphragm 20. As the pressure compensator diaphragm 20 collapses and filling media is transferred to the occlusive cuff 2, an equal volume of fluid is transferred into the compensator shell 21. This fluid transfer prevents a vacuum from forming within the compensator shell 21 which might prevent proper collapse of the pressure compensator diaphragm 20. Fluid transfer to the compensator shell 21 is facilitated by the collapse of a flexible compensator dome 24 on the outer surface of the compensator shell 21 as shown in FIGS. 5C and 5D. Expansion of the pressure compensator diaphragm 20 causes fluid transfer from the compensator shell 21 and re-expansion of the compensator dome 24 as shown in FIGS. 5A and 5B. At the time of surgical implantation, the compensator shell 21 is filled with an isotonic filling solution such as normal saline via a needle inserted into the septum 9.

The pressure compensator 4 components may all be manufactured from silicone rubber. Wear between opposing surfaces of the pressure compensator diaphragm 20 may be minimized using the low-coefficient of friction surface treatment described above for the occlusive cuff 2.

Control Mechanism

Tension applied to the pressure compensator diaphragm 20 is supplied by a control mechanism 3 implanted in the scrotum of the male or in the abdominal wall of the female or in a miniaturized version within the labia of the female. See e.g. FIGS. 6A to 7C. Depression of an activation button 25 (e.g. 5) on the control mechanism 3 through the intact skin causes a spring force to retract the pressure compensator diaphragm 20 and apply a constant pressure to the urethra 13 which it encircles. Depression of a deactivation button 26 (e.g. 6) also located on the control mechanism 3, releases the spring force from the pressure compensator diaphragm 20 and removes pressure from the urethra 13.

Embodiments of various control mechanisms are described in great detail in U.S. Pat. No. 8,007,429 B2 VESSEL OCCLUSIVE DEVICE AND METHOD FOR OCCLUDING A VESSEL. One of these embodiments is further described in below.

Pulley 27 counter-rotation is accomplished when the user depresses the deactivation button 26 exiting the control mechanism 3. A cable 28 wraps around the small pulley 29 at one end and the radiused base of the deactivation button 26 at its other end as shown in FIGS. 6A and 6B. As the deactivation button 26 advances, the distance the cable 28 is pulled, is magnified relative to the distance the deactivation button 26 is depressed.

When the deactivation button 26 is depressed to its full extent, a détente pin 30 contained within the deactivation button 26 engages a lever 31, which prevents the deactivation button 26 from returning to its original extended position as shown in FIG. 7A-7C. The lever 31 is biased by a spring 32 captured between the lever 31 and a silicone rubber boot 7 (see e.g. FIG. 1) surrounding the control mechanism 3. As the deactivation button 26 is depressed, the deactivation button dome 33 of the flexible silicone boot 7 deforms with the force applied to it, but rebounds to its original shape when the force is removed. In this way, the occlusive cuff 2 is held in a condition which does not compress the urethra. Rebounding of the deactivation button dome 33 prevents tissue capsule formation, which normally forms around implanted devices over time, restricting movement of the deactivation button 26.

When the patient desires to return to a continent state with the urethra 13 compressed, the silicone boot 7 is depressed over the lever 31 as shown in FIG. 7C. See e.g. arrow, activation button 25 in FIG. 7C. This disengages the lever 31 from the détente pin 30, allowing the deactivation button 26 to return to an extended position under the bias of a constant force spring 34 nested within the pulley 27.

FIG. 11 is a schematic view of one embodiment of a hydraulic urethral occlusive device implanted in a human male subject. In particular, FIG. 11 shows the anatomical placement for example of the hydraulic urethral occlusive device 10 including the occlusive cuff 2, the control mechanism 3, and the pressure compensator 4. It will be appreciated that any of the hydraulic urethral occlusive devices described herein, including their accompanying components such as the occlusive cuff, pressure compensator, control mechanism, and conduit tubes, may be similarly implanted as shown in FIG. 11. Placement of the pressure compensator 4 may be made in the abdominal subcutaneous tissue, tissue of the thigh or in the pre-vesical space between the urinary bladder and pubic bone. FIG. 11 shows the pressure compensator 4 placed in the abdominal subcutaneous tissue. As described above, increases in intra-abdominal pressure can be transferred hydrostatically to the bladder and, when the bladder pressure exceeds the urethral closure pressure, urinary leakage occurs. Increases in intra-abdominal pressure may be caused by stressful events such as for example, sneezing, coughing, or laughing. Pressurization of the occlusive cuff 2 to occlude the urethra occurs when the diaphragm inside the pressure compensator 4 collapses under the influence of the tension cord, e.g. 19, attached to the tensioning mechanism contained within the control mechanism 3. The control mechanism 3 can establish for example about 60-80 cm $H_2O$ of urethral occlusive pressure when the control mechanism 3 is in the activated condition. The urethral occlusive pressure range can minimize urinary leakage in the situations where the natural urinary sphincter has been damaged by disease or trauma.

FIGS. 12A to 12D show views of another embodiment of a pressure compensator 400 with a hollow shell 421, which may be flexible and which may be resilient. It will be appreciated that the pressure compensator 400 may be implemented with any of the control mechanisms and occlusive cuffs described herein, and for purposes of discussion the pressure compensator 400 is described with respect to the control mechanism 3 and occlusive cuff 2 of FIG. 1 or FIG. 11.

In FIGS. 12A to 12D, the pressure compensator 400 is a structure that may be attached to control mechanism 3 via a flexible conduit tube 418, 10. A tension cord 419 travels from the control mechanism 3 through the conduit tube 418 to the apex of the pressure compensator diaphragm 420. The pressure compensator diaphragm 420 can be a thin-walled, bullet-shaped diaphragm which operates between an expanded and collapsed condition. Tension applied to the tension cord 419 by the control mechanism 3 collapses the pressure compensator diaphragm 420, and pressurizes the filling media contained within the filling media volume 423 (see e.g. FIGS. 12B to 12C). The fluid in the filling media volume 423 is then transferred to the occlusive cuff 2 which inflates to occlude the urethra. As the diaphragm 420 collapses, the flexible wall of the shell 421 can also collapse some in response to vacuum created within the fluid volume 422.

The pressure generated within the pressure compensator diaphragm 420 can be determined by its cross-sectional area and the force applied to the tension cord 19 according to the equation:

Pressure=Force/Cross-sectional Area

When tension is released from the tension cord 419, the resilience of the compressed urethral tissue forces filling media out of the occlusive cuff 2 and re-expands the pressure compensator diaphragm 420 to the position shown in FIGS. 12A and 12B.

The pressure compensator diaphragm 420 is contained within a compensator shell 421 which may be of a flexible material that is compatible for implantation, and which may be resilient. The fluid volume 422 is contained within the compensator shell 421. The fluid volume 422 surrounds and is separated from the filling media volume 423 contained within the pressure compensator diaphragm 420. The pressure compensator can also include infusion ports 426, 428 for the fluid volume 422 and filling media volume 423, respectively.

In the embodiment of FIGS. 12A to 12D, the compensator shell 421 surrounding the pressure compensator diaphragm 420 may also be externally compressed to provide a greater pressure within the pressure compensator diaphragm 420, such as for example pressures higher than the 60-80 cm $H_2O$ as described above. In some embodiments, the increased pressure may be within the range of about 80-200 cm $H_2O$. Such pressures may be useful and suitable to prevent urinary leakage during even more stressful events. In FIGS. 12A to 12D, there are no obstructions in the hydraulic flow paths between the pressure compensator 400, control mechanism 3 and occlusive cuff 2. Pressure increases within the pressure compensator 400 can be directly transferred to the occlusive cuff. When external pressure is removed from the pressure compensator 4, the occlusive pressure can return to its usual, e.g. resting, pressure for example at about 60 to 80 cm $H_2O$.

In contrast to the semi-rigid pressure compensator 4 above, the pressure compensator 400 may be constructed as a hollow-shelled, flexible structure to sometimes facilitate additional hydraulic pressure transfer from the pressure compensator to the occlusive cuff.

In some embodiments, the compensator shell 421, diaphragm 420, diaphragm mount, control mechanism outer covering (e.g. boot), occlusive cuff components are silicone or a similar material. In some embodiments, the conduit tube 10, 418 (e.g. from the pressure compensator 400 to control mechanism 3) has an outer silicone layer, a central metal coil, and an inner expanded polytetrafluoroethylene (ePTFE) layer. In some embodiments, the conduit tube between the occlusive cuff and the control mechanism is silicone. In some embodiments, the tension cord 419 is a polytetrafluoroethylene material such as a Teflon® coated polyester. In some embodiments, inner components of the control mechanism 3 may be constructed using a mixture of titanium, stainless steel, and ultra-high molecular weight polyethylene.

FIGS. 13A and 13B show embodiments of a hydraulic urethral occlusive device implanted in a human male subject, and which may implement the pressure compensator 400 (shown schematically) of FIGS. 12A to 12D. It will be appreciated that any of the hydraulic urethral occlusive devices described herein, including their accompanying components such as the occlusive cuff, pressure compensator, control mechanism, and conduit tubes, may be similarly implanted as shown in FIGS. 13A and 13B.

FIG. 13A shows the pressure compensator 400 placed in a subcutaneous location, such as in the abdominal subcutaneous tissue. Pressure compensator placement in the abdominal subcutaneous tissue can allow the subject or patient to manually compress the pressure compensator 400 through the abdominal skin. In so doing, the urethral closure pressure can be increased above the baseline pressure of, for example 60-80 cm $H_2O$, and can be increased such as for example in anticipation of particularly stressful events such as sneezing, coughing, or laughing. Removal of this manual compression allows a return to the normal resting urethral pressure, e.g. above the baseline pressure such as about 60-80 cm $H_2O$.

FIG. 13B shows the pressure compensator 400 placed in a pre-vesical space, such as between the pubic bone 402 and the bladder 404. Pressure compensator placement in the pre-vesical space between the bladder 404 and pubic bone 402 can allow bladder pressure increases to be transmitted to the pressure compensator 400 in real-time. In so doing, the occlusive cuff 2 could respond automatically to increases in abdominal pressure without manual intervention, such as in FIG. 13A.

The use of the pressure compensator 400 with a hollow flexible shell, e.g. 421, can allow for transfer of hydraulic pressure directly to the cuff, where the filling volume 423 and fluid volume 422 can be constructed and arranged for example as a reservoir within a reservoir configuration. The placement for example in a pre-vesical space can allow for a real time response to increases in bladder pressure, such as for example above a baseline occlusive pressure.

Post-Implantation Refilling/Repressurization

From clinical history with other commercially available artificial urinary sphincters (AUS), it is noted that post-implantation pressures applied to the urethra are frequently inadequate to provide improved continence. In these cases, the only recourse is for the patient to use other means to manage their incontinence, or to have the implanted AUS removed and replaced with one of a higher pressure. Increased risk of surgical mortality and morbidity exists with any additional surgical intervention.

If patients implanted with the hydraulic urethral occlusive device continue to leak urine, the device may be re-pressurized to a higher pressure to reduce this degree of leakage. Re-pressurization is performed by accessing the needle port 8 with a needle to allow fluid communication between the hydraulic urethral occlusive device interior and a syringe attached to a pressure transducer. The pressure transducer is used to confirm the pressure infused into the hydraulic urethral occlusive device interior by the syringe. Alternately, the needle may be attached to a bag of saline which may then be elevated to provide a water column pressure equivalent to the pressure desired within the hydraulic urethral occlusive device interior. This procedure may be performed multiple times until the patient achieves the desired degree of continence.

The pressure maintained in the device may be defined as Pressure=Force/Cross-sectional Area as given above. The Cross-sectional Area is the fixed value established by the pressure compensator diaphragm 20. However, the force generated by the constant force spring 34 is not perfectly constant and increases gradually with increased rotational displacement of the pulley 27 in which the constant force spring 34 is contained. The incremental fluid volume infused into the hydraulic urethral occlusive device interior during refilling/repressurization increases this rotational displacement to incrementally increase the interior pressure.

FIG. 14 shows another embodiment of post-implantation adjustment, for example to increase or decrease occlusive pressure, by way of using a retrograde perfusion technique.

Occlusive pressure may be increased by the incremental addition of volumes of hydraulic filling solution (e.g. normal saline), which may be known, fixed volumes of solution. Rather than measuring the achieved pressure as described above, a retrograde perfusion technique 500 may be employed to measure the urethral closure pressure directly. Retrograde perfusion can be performed using the following procedure and materials to determine a patient's urethral opening pressure (e.g. urethral occlusive pressure) once a satisfactory degree of continence is achieved.

As shown in FIG. 14, retrograde perfusion can be performed using a sterile saline intravenous (IV) bag 502, a drip infusion set 504, a urethral infusion catheter 506, a measuring device 508 such as a measuring tape, and an IV stand 510.

The retrograde perfusion materials, apparatus can be assembled as shown in FIG. 14. Once a patient has achieved a desired degree of continence, the hydraulic urethral occlusive device, e.g. as shown in FIGS. 1, 8, 11, and 13, can be activated. The scrotum and control mechanism 3 can be moved back and forth several times. The urethral infusion catheter can be inserted manually into the distal urethra and the penis grasped to affect a fluid tight seal between catheter and urethra. With infusion set clamps opened, the IV bag can be slowly elevated to the point at which dripping in the drip chamber is first seen. The column height H can be measured and then recorded as the urethral opening pressure. It will be appreciated that any of the hydraulic urethral occlusive devices described herein, including their accompanying components such as the occlusive cuff, pressure compensator, control mechanism, and conduit tubes, may be similarly used in a retrograde perfusion technique.

Alternative Electro-Mechanical Control Mechanism

The mechanical control mechanism 3, described above, may be replaced by a closed loop, electro-mechanical, servo-control system. This system also has occlusive cuff 2 and pressure compensator diaphragm 20 as described above, a pulley 35, rotary actuator such as a motor 36, microprocessor based control mechanism 37, power supply 38, and separate urethral 39 and abdominal 40 pressure sensing elements. In this embodiment, the rotary actuator 36 turns the pulley 35 which, in turn, takes up and applies load to the tension sutures 41 to pressurize the pressure compensator diaphragm 20 and occlusive cuff 2 to occlude the urethra 13. See e.g. FIG. 8. It is to be appreciated that a linear actuator such as a lead screw may be used in place of a rotary actuator.

In its resting state, the pulley 35 is biased so that the pressure compensator diaphragm 20 applies 0 to 20 cm $H_2O$ pressure to the urethra 13. This pressure range is adequate to prevent urinary leakage during normal, unstressful activities. Urethral pressure is continuously or intermittently monitored by a urethral pressure sensing element 39 situated between the occlusive cuff 2 and the outer surface of the urethra 13. Abdominal or bladder pressure is monitored continuously or intermittently by a pressure sensor 40 implanted within the abdominal cavity, within the abdominal wall, within the bladder or within the bladder wall.

As bladder filling occurs, bladder pressure increases within the range of 20-60. Sensing this pressure increase, the abdominal/bladder pressure sensor 40 signals the control mechanism 37 to turn the motor 36 on and cause the pulley 35 to rotate and affect a rise in urethral pressure. When the urethral pressure sensing element 39 detects that urethral pressure is 60-80 cm $H_2O$, the motor 36 is turned off and the pulley 35 held in position to prevent any further pressure increase or decrease. Once the abdominal/bladder pressure reduces to 20 cm $H_2O$ or less, the control mechanism 37 is again signaled to allow the rotary actuator 36 to reverse direction and reduce tension on the traction sutures 41 until urethral pressures between 0 and 20 cm $H_2O$ are achieved.

Stressful events such as coughing, sneezing, laughing, etc. can often cause abdominal/bladder pressures spikes in excess of 60 cm $H_2O$. Pressure rise times of 35 msec and elevated pressure durations of approximately 100 msec have been recorded. Sensing these pressure levels, the control mechanism 37 causes the rotary actuator 36 to turn on and rotate the pulley 35 to affect a rise in urethral pressure of as much as 120 cm $H_2O$. When abdominal/bladder pressure declines to 20 cm $H_2O$ or less, the control mechanism 37 allows the rotary actuator 36 to reverse direction and reduce tension on the traction sutures 41 until urethral pressures between 0 and 20 cm $H_2O$ are achieved.

When the user wishes to void urine, a switch on the control mechanism 37 is manually activated through the skin. This action causes the pulley 35 to free-wheel, reducing traction suture 41 tension until a 0 cm $H_2O$ urethral pressure is achieved. The user then voids urine through the unobstructed urethra 13. The user may then be required to manually depress the switch again to return the device to its resting mode or the device will be programmed to automatically return to its resting mode within 3-5 minutes.

Referring to FIGS. 9, 10A, and 10B, another embodiment for closing or otherwise retaining and/or locking the occlusive cuff in place is shown. FIG. 9 is a partial perspective view of another embodiment of an occlusive cuff 102 not encircling a urethra and shown in a flat condition. FIG. 10A is a partial view showing the occlusive cuff 102 of FIG. 9 shown encircling a urethra but not in the fully clipped position. FIG. 10B is a partial view showing the occlusive cuff 102 of FIG. 9 shown encircling a urethra in the fully clipped position.

As described with respect to the earlier Figures, the occlusive cuff 102 can have a thin-walled, expandable pouch 111 to which is affixed a semi-flexible cuff backing strip 112. When encircling the urethra 113 (see e.g. FIGS. 10A and 10B), the fluid-tight expandable pouch 11 may be alternately expanded or deflated by infusion of a suitable filling media such as isotonic saline or radiopaque contrast media. Inflation occurs through a flexible input tube 114. In one embodiment, the flexible input tube 114 can extend from connector end 119, for example in a direction along the length of the expandable pouch 111 and backing strip 112, which may help during manipulation and during implantation. The occlusive cuff 102 with the expandable pouch 111 may be inflated similar to that shown in FIG. 3. When the expandable pouch 111 is inflated, the pressure exerted on the urethra 113 is sufficient to prevent or minimize urinary leakage. Historical clinical evidence suggests that this pressure should be in the range of 60-80 cm $H_2O$ to provide adequate leak resistance without causing undue urethral atrophy or tissue erosion. When the expandable pouch 111 is deflated, pressure is removed from the urethra 113 to allow normal, unobstructed urinary drainage. The cuff backing strip 112 is positioned on the expandable pouch 111 surface away from the urethral surface and acts to maximize urethral occlusion efficiency by minimizing radial expansion of the expandable pouch 111 away from the urethra 113. Sizing Detents 115 can also be positioned on the cuff backing strip 112 to allow the occlusive cuff 102 to be sized to accommodate anatomical variations in urethral circumferences as may occur in the human population. Clinical experience indicates that the range of urethral circumferences in the human male population ranges from about 3.5 cm to about 5.0 cm. Sizing indicators 116 may be associated with the detents 115 to provide the surgeon with urethral circumference information.

When the occlusive cuff 102 is surgically wrapped around the urethra 113, the free end of the occlusive cuff 102 may retained by a retaining member 117. The retaining member 117 in some embodiments can be a t-bar that may be inserted through any one of the openings 118 on the backing strip 112. The openings 118 on the backing strip 112 can correspond to a size indicated by the indicators 116 and/or the sizing detents 115. In some embodiments, the retaining member 117 can be a stainless steel t-bar, or may be a plastic material, or other suitably rigid material, and is also a material suitable for implant in a patient or subject.

It will be appreciated that any of the indicators 116 and/or sizing detents 115 may not be employed, and it will be appreciated that the specific t-bar configuration as shown in the figures is exemplary of the retaining member 117, is not meant to be limiting, and may be suitably modified.

When the occlusive cuff 102 is surgically wrapped around the urethra 113, the backing strip 112 can be advanced around the connecting end 119 and the retaining member 117 then secured through an opening 118 on the backing strip 112 to provide a close fit between the occlusive cuff 102 and urethra 113. In one embodiment, the connecting end 119 can have a ramped side on which the retaining member 117 is disposed, and which may help during manipulation and during implantation and closure of the cuff 102.

The structure shown in FIGS. 9, 10A, and 10B can also allow for adjustability and which provides a positive locking system to prevent the cuff from becoming accidentally disengaged. It will also be appreciated that the occlusive cuff closure shown in FIGS. 9, 10A, and 10B can incorporate a suitable retaining member, e.g. 117, such as a stainless steel t-bar which engages openings in the occlusive cuff 102, which may be an elastomeric, silicone occlusive cuff backing. In some embodiments, the openings 118 can be spaced to allow the occlusive cuff to accommodate urethras within a circumference range of about 3.0 cm to about 5.0 cm in about 0.5 cm increments.

It will be appreciated that any of aspects 1 to 14 may be combined with any of aspects 15 to 22, and any of aspects 15 to 18, 21, and 22 may be combined with any of aspects 19 and 20.

Aspect 1. An implantable occlusive device, comprising: an occlusive cuff; a control mechanism; and a pressure compensator, the control mechanism is in fluid communication with the occlusive cuff, through attachment via a flexible tube, the control mechanism is in fluid communication with an inner portion of the pressure compensator, through attachment via a flexible conduit, the control mechanism including an activation button and a deactivation button, the activation button upon depression, hydraulically inflates with hydraulic fluid the occlusive cuff to apply a preset occlusive pressure on the tubular body, the deactivation button upon depression, hydraulically evacuates the hydraulic fluid from the occlusive cuff to remove the preset occlusive pressure on the tubular body.

Aspect 2. The device of aspect 1, wherein the occlusive cuff is adjustable to encircle a urethra.

Aspect 3. The device of aspect 1 or 2, wherein the occlusive cuff comprises an expandable pouch affixed to a cuff backing strip, the expandable pouch is inflatable when the hydraulic fluid enters the expandable pouch through the flexible tube so as to apply the preset urethral pressure, and the expandable pouch is deflatable when the hydraulic fluid evacuates from the expandable pouch through the flexible tube so as to remove the preset urethral pressure.

Aspect 4. The device of any of aspects 1 to 3, wherein the occlusive cuff comprises sizing detents, a free end, and a locking clip, the free end is insertable through the locking clip to lock the occlusive cuff to one of the sizing detents.

Aspect 5. The device of any of aspects 2 to 4, further comprising a retaining member at one end of the occlusive cuff, the retaining member is engageable with an opening through the cuff backing strip.

Aspect 6. The device of any of aspects 1 to 5, wherein the control mechanism is encapsulated by a silicone boot.

Aspect 7. The device of any of aspects 1 to 6, wherein the control mechanism comprises a septum.

Aspect 8. The device of any of aspects 1 to 7, further comprising a tension cord that travels from the control mechanism to a diaphragm defines a filling media volume inside the pressure compensator, the diaphragm is configured to operate between an expanded condition and a collapsed condition, the control mechanism configured to apply tension to the tension cord to collapse the diaphragm and the filling media volume into the collapsed condition, where the hydraulic fluid transfers to the occlusive cuff to inflate the occlusive cuff, and the control mechanism configured to release tension from the tension cord to evacuate the hydraulic fluid from the occlusive cuff, where the hydraulic fluid transfers to the pressure compensator to expand the diaphragm and the filling media volume to the expanded condition.

Aspect 9. The device of aspect 8, wherein the pressure compensator further comprises a shell, a fluid volume contained within the shell and that surrounds and is separated from the filling media volume, as the diaphragm is collapsed, fluid transfers into the fluid volume, and as the diaphragm expands, fluid transfers out of the fluid volume.

Aspect 10. The device of aspect 9, wherein the pressure compensator further comprises a dome, the dome is configured to allow fluid to transfer into the fluid volume when the diaphragm collapses and allow fluid to transfer out of the fluid volume when the diaphragm expands.

Aspect 11. The device of aspect 9 or 10, wherein the inner portion of the pressure compensator contains a fluid different from a fluid in the fluid volume.

Aspect 12. The device of any of aspects 1 to 11, wherein the pressure compensator comprises a septum.

Aspect 13. The device of any of aspects 1 to 12, wherein the control mechanism includes an electro mechanical control.

Aspect 14. The device of any of aspects 1 to 13, wherein the control mechanism is configured to incrementally increase occlusive pressure on the tubular body.

Aspect 15. A method of tubular body occlusion, comprising: collapsing a diaphragm inside a pressure compensator shell to transfer hydraulic fluid to an occlusive cuff, the transfer of hydraulic fluid being via conduits in fluid communication with a control mechanism; pressurizing the occlusive cuff as a result of the transfer of hydraulic fluid from the collapsing of the diaphragm inside the pressure compensator shell; occluding a tubular body surrounded by the occlusive cuff as a result of pressurizing of the occlusive cuff; and during a desired state of non-occlusion, depressurizing the occlusive cuff to transfer the hydraulic fluid from the occlusive cuff to the inside of the pressure compensator to thereby expand the diaphragm, and during a desired state of occlusion, repressurizing the occlusive cuff, by repeating the steps of collapsing, pressurizing, and occluding.

Aspect 16. The method of aspect 15, wherein the control mechanism is a mechanical control mechanism.

Aspect 17. The method of aspect 15 or 16, wherein the control mechanism is an electro mechanical control mechanism.

Aspect 18. The method of any of aspects 15 to 17, further comprising incrementally increasing pressure on the tubular body.

Aspect 19. The device of any of aspects 1 to 9 and 11, wherein the pressure compensator has a hollow flexible shell.

Aspect 20. The device of aspect 19, wherein the pressure compensator including its shell is configured for placement in one of a subcutaneous location or a pre-vesical location.

Aspect 21. The method of any of aspects 15 to 18, further comprising placing the pressure compensator in one of a subcutaneous location or a pre-vesical location.

Aspect 22. The method of any of aspects 15 to 18 and 21, further comprising repressurizing the device or determining the urethral occlusive pressure using a retrograde perfusion technique.

While the embodiments have been described in terms of various specific embodiments, those skilled in the art will recognize that the embodiments can be practiced with modification within the spirit and scope of the claims.

The invention claimed is:

1. An implantable occlusive device, comprising:
an occlusive cuff;
a control mechanism; and
a pressure compensator having a hollow flexible shell and being configured for placement in one of a subcutaneous location or a pre-vesical location, wherein the subcutaneous location includes abdominal subcutaneous tissue between a pubic bone and abdominal skin and the pre-vesical location is disposed between a bladder and the pubic bone,
wherein the control mechanism is in fluid communication with the occlusive cuff, through attachment via a flexible tube,
the control mechanism is in fluid communication with an inner portion of the pressure compensator, through attachment via a flexible conduit, and the control mechanism is mechanically connected to a diaphragm inside the pressure compensator, and
the control mechanism includes an activation button and a deactivation button, the activation button upon depression, hydraulically inflates with hydraulic fluid the occlusive cuff to apply a preset occlusive pressure on a tubular body, the deactivation button upon depression, hydraulically evacuates the hydraulic fluid from the occlusive cuff to remove the preset occlusive pressure on the tubular body,
wherein when the pressure compensator is placed in the subcutaneous location, a force applied through the abdominal skin compresses the pressure compensator, thereby increasing a pressure in the pressure compensator and the occlusive cuff, and
when the pressure compensator is placed in the pre-vesical location, a force applied by an increase in bladder pressure compresses the pressure compensator, thereby increasing a pressure in the pressure compensator and the occlusive cuff.

2. The device of claim 1, wherein the occlusive cuff is adjustable to encircle a urethra.

3. The device of claim 2, wherein the occlusive cuff comprises an expandable pouch affixed to a cuff backing strip, the expandable pouch is inflatable when the hydraulic fluid enters the expandable pouch through the flexible tube so as to apply a preset urethral pressure, and the expandable pouch is deflatable when the hydraulic fluid evacuates from the expandable pouch through the flexible tube so as to remove the preset urethral pressure.

4. The device of claim 3, further comprising a retaining member at one end of the occlusive cuff, the retaining member is engageable with an opening through the cuff backing strip.

5. The device of claim 1, wherein the occlusive cuff comprises sizing detents, a free end, and a locking clip, the free end is insertable through the locking clip to lock the occlusive cuff to one of the sizing detents.

6. The device of claim 1, wherein the control mechanism is encapsulated by a silicone boot.

7. The device of claim 1, wherein the control mechanism comprises a septum.

8. The device of claim 1, further comprising a tension cord that travels from the control mechanism to the diaphragm that mechanically connects the control mechanism and the diaphragm and defines a filling media volume inside the pressure compensator, the diaphragm is configured to operate between an expanded condition and a collapsed condition, the control mechanism configured to apply tension to the tension cord to collapse the diaphragm and the filling media volume into the collapsed condition, where the hydraulic fluid transfers to the occlusive cuff to inflate the occlusive cuff, and the control mechanism configured to release tension from the tension cord to evacuate the hydraulic fluid from the occlusive cuff, where the hydraulic fluid transfers to the pressure compensator to expand the diaphragm and the filling media volume to the expanded condition.

9. The device of claim 8, wherein the pressure compensator further comprises a shell, a fluid volume contained within the shell and that surrounds and is separated from the filling media volume, as the diaphragm is collapsed, fluid transfers into the fluid volume, and as the diaphragm expands, fluid transfers out of the fluid volume.

10. The device of claim 9, wherein the pressure compensator further comprises a dome, the dome is configured to allow fluid to transfer into the fluid volume when the diaphragm collapses and allow fluid to transfer out of the fluid volume when the diaphragm expands.

11. The device of claim 9, wherein the inner portion of the pressure compensator contains a fluid different from a fluid in the fluid volume.

12. The device of claim 1, wherein the pressure compensator comprises a septum.

13. The device of claim 1, wherein the control mechanism includes an electro mechanical control.

14. The device of claim 1, wherein the control mechanism is configured to incrementally increase occlusive pressure on the tubular body.

15. A method of tubular body occlusion, comprising:
collapsing a diaphragm inside a pressure compensator shell to transfer hydraulic fluid to an occlusive cuff, the transfer of hydraulic fluid being via conduits in fluid communication with a control mechanism, wherein the control mechanism is mechanically connected to the diaphragm, wherein the pressure compensator shell is placed in one of a subcutaneous location or a pre-vesical location, the subcutaneous location including abdominal subcutaneous tissue between a pubic bone and abdominal skin and the pre-vesical location being disposed between a bladder and the pubic bone;
pressurizing the occlusive cuff as a result of the transfer of hydraulic fluid from the collapsing of the diaphragm inside the pressure compensator shell;
one of:
  compressing the pressure compensator when a force is applied through the abdominal skin and the pressure compensator is in the subcutaneous location, and
  compressing the pressure compensator when a force is applied by an increase in bladder pressure and the pressure compensator is in the pre-vesical location;
occluding a tubular body surrounded by the occlusive cuff as a result of pressurizing of the occlusive cuff, wherein the occluding includes incrementally increasing pressure on the tubular body; and
during a desired state of non-occlusion, depressurizing the occlusive cuff to transfer the hydraulic fluid from the occlusive cuff to the inside of the pressure compensator to thereby expand the diaphragm, and during a desired state of occlusion, repressurizing the occlusive cuff, by repeating the steps of collapsing, pressurizing, and occluding.

16. The method of claim 15, wherein the control mechanism is a mechanical control mechanism.

17. The method of claim 15, wherein the control mechanism is an electro mechanical control mechanism.

18. The method of claim 15, further comprising repressurizing the device or determining the urethral occlusive pressure using a retrograde perfusion technique.

19. An implantable occlusive device, comprising:
an occlusive cuff that is adjustable to encircle a urethra;
a control mechanism;
a pressure compensator having a hollow flexible shell and being configured for placement in a subcutaneous location, wherein the subcutaneous location includes abdominal subcutaneous tissue between a pubic bone and abdominal skin; and
a retaining member at one end of the occlusive cuff,
wherein the control mechanism is in fluid communication with the occlusive cuff, through attachment via a flexible tube,
the control mechanism is in fluid communication with an inner portion of the pressure compensator, through attachment via a flexible conduit, the control mechanism being mechanically connected to a diaphragm inside the pressure compensator, and
the control mechanism includes an activation button and a deactivation button, the activation button upon depression, hydraulically inflates with hydraulic fluid the occlusive cuff to apply a preset occlusive pressure on a tubular body, the deactivation button upon depression, hydraulically evacuates the hydraulic fluid from the occlusive cuff to remove the preset occlusive pressure on the tubular body,
the occlusive cuff comprises an expandable pouch affixed to a cuff backing strip, the expandable pouch is inflatable when the hydraulic fluid enters the expandable pouch through the flexible tube so as to apply a preset urethral pressure, and the expandable pouch is deflatable when the hydraulic fluid evacuates from the expandable pouch through the flexible tube so as to remove the preset urethral pressure, and
the retaining member is engageable with an opening through the cuff backing strip,
wherein when the pressure compensator is placed in the subcutaneous location, a force applied through the abdominal skin compresses the pressure compensator, thereby increasing a pressure in the pressure compensator and the occlusive cuff.

* * * * *